United States Patent [19]
Hokama

[11] Patent Number: 5,279,572
[45] Date of Patent: Jan. 18, 1994

[54] INDWELLING INTRAVENOUS NEEDLE WITH TWO BLOOD-BACKFLOW PASSAGE ROUTES

[76] Inventor: Yasuo Hokama, 29-8, Shuritairacho 1-chome, Naha City, Okinawa Prefecture 903, Japan

[21] Appl. No.: 878,777

[22] Filed: May 5, 1992

[30] Foreign Application Priority Data

Dec. 3, 1991 [JP] Japan ................................ 3-357462

[51] Int. Cl.$^5$ .............................................. A61M 5/178
[52] U.S. Cl. ................................... 604/168; 604/272
[58] Field of Search .................... 604/40, 42, 44, 45, 604/52, 53, 164, 166, 168, 239, 263, 264, 272, 43, 51, 165, 167, 169, 170, 273-274

[56] References Cited

U.S. PATENT DOCUMENTS

| | | | |
|---|---|---|---|
| 3,081,770 | 3/1963 | Hunter | 604/32 |
| 3,714,945 | 2/1973 | Stanley | 604/164 |
| 4,020,835 | 5/1977 | Nordstrom et al. | 604/272 |
| 4,186,750 | 2/1980 | Patel | 604/272 |
| 4,203,436 | 5/1980 | Grimsrud | 604/44 |
| 4,850,373 | 7/1989 | Zatloukal et al. | 604/264 |
| 4,894,052 | 1/1990 | Crawford | 604/53 |

FOREIGN PATENT DOCUMENTS

| | | | |
|---|---|---|---|
| 2703087 | 7/1978 | Fed. Rep. of Germany | 604/44 |
| 3522782 | 1/1987 | Fed. Rep. of Germany | 604/44 |

*Primary Examiner*—C. Fred Rosenbaum
*Assistant Examiner*—Mark Bockelman
*Attorney, Agent, or Firm*—Anderson Kill Olick & Oshinsky

[57] ABSTRACT

An indwelling intravenous needle having two blood backflow passage routes. One is an internal cavity of a metallic internal needle, which is the basic construction of an indwelling intravenous needle of a conventional type. The other is being a groove provided on the surface of the internal needle extending from the proximal cutting-edge to the internal-needle base is disclosed. By visually observing blood backflows in these two passage routes separately, the indwelling intravenous needle can be pierced into the vein accurately, quickly and safely.

2 Claims, 4 Drawing Sheets

:::: {.flushright}
5,279,572
::::

INDWELLING INTRAVENOUS NEEDLE WITH TWO BLOOD-BACKFLOW PASSAGE ROUTES

BACKGROUND OF THE INVENTION (a) Field of the Invention

This invention relates generally to medical apparatus, and more particularly to a specific construction of an internal needle as a component of an indwelling intravenous needle.

(b) Description of Related Art

In the following, the construction of a commonly used indwelling intravenous needle will be described, referring to FIG. 2, an enlarged side view of such a needle. Reference numeral 1 refers to a tip of a cutting edge of a hollow internal needle 3, made of a metal, of an indwelling intravenous needle; the tip being beveled to make it easy for the needle 3 to pierce into the blood vessel. Numeral $4_1$ refers to an internal-needle base, made of a hard synthetic resin, of the internal needle 3; the inside thereof being formed wide so that the blood flowing backward from the inner bore 5 of the internal needle 3 can be collected.

Numeral 2 refers to a hollow external needle, made of a resilient translucent synthetic resin, covering the internal needle 3 in the vicinity of the rear of the beveled cutting edge 1 of the internal needle 3. The rear end of the external needle 2 is opened so that the tip of the internal needle base $4_1$ can be inserted, and that the blood or medicine passing through the inner bore of the external needle 2 is allowed to flow after removal of the internal needle 3 by connecting to a duct (not shown). An external-needle base $4_2$ is made of a synthetic resin of the same type as that of the internal-needle base $4_1$.

Now, description will be made on how to use the indwelling intravenous needle of the conventional type having the aforementioned construction. The indwelling intravenous needle in the state shown in FIG. 2 is pierced into the vein. As the internal needle 3 is pierced, and the blood is visually observed flowing backward in the inner bore 5 to point P on the internal-needle base $4_1$' the external needle 2 is left pierced in the vein. When the needle of the shape shown in FIG. 2 is pierced in the blood vessel, however, various problems are encountered, as shown in FIGS. 5(a)–(e). FIG. 5(a)–(e) is a schematic side view of assistance in explaining various problems encountered when the indwelling intravenous needle of the conventional type is pierced into the blood vessel. The indwelling intravenous needle is held in hand and pierced into the skin 9, advanced to a certain length, then the tip 1 is directed toward the vein wall 10, and further advanced until the cutting edge is felt reaching the vein cavity 11. At this point of time, the internal needle base $4_1$ is checked to see the state of the blood flow. If it is visually confirmed that no blood is flowing backward at point P (see FIG. 2) of the internal-needle base $4_1$ it means that the indwelling intravenous needle just comes in contact with the vein, or it has gone in a different direction from the vein. In the former case, the needle should be advanced more deeply, and in the latter case, the procedure must be repeated from the subcutaneous position. This state is shown in FIG. 5(a).

Next, if the blood is found flowing backward at point P of the internal-needle base $4_1$ it means the direction of the needle is correct, so the indwelling intravenous needle is penetrated further until the tip of the external needle 2 is felt reaching the vein cavity 11, then the internal needle 3 is extracted. At this point in time, if the blood is not found flowing backward to the external needle 2, it means that only the cutting edge of the internal needle 3 has reached the vein cavity 11 due to insufficient penetration. This state is shown in FIG. 5(b). In this state, if another attempt is made to cause the internal needle 3 to pierce again by replacing the internal needle 3 into the external needle 2, the attempt would fail. This is due to the swelling of an area around the vein, caused by the hypodermic bleeding flowing through the hole previously cut by the internal needle 3.

To avoid the state shown in FIG. 5(b) noted above, the entire indwelling intravenous needle is further advanced by the length of the cutting edge after the blood is found flowing backward at point P of the internal-needle base $4_1$. If the blood continues to flow backward at point P of the internal-needle base $4_1$ there is a likelihood that the external needle 2 can be smoothly advanced in the vein after the internal needle 3 is extracted. This is an ideal treatment. This state is shown in FIG. 5(c).

The blood, however, may flow backward at point P of the internal-needle base $4_1$ even in the state shown in FIG. 5(d) where the cutting-edge tip is pierced through the lower vein wall 10, with only the root 6 thereof left in the vein cavity 11. In this state, even when the blood back-flow in the external needle 2 is visually confirmed after the internal needle 3 has been extracted, any attempt to advance the external needle 2 could result in the external needle 2 hitting against the lower vein wall 10. Since areas around the vein wall 10 are swollen by the hypodermic bleeding flowing through the hole previously pierced by the internal needle 3, it is difficult to advance the external needle 2 into the vein cavity 11. In short, this could also lead to a failure.

Furthermore, if the blood back-flow at point P of the internal-needle base $4_1$ is discontinued halfway, it means that the entire internal needle cutting edge goes all the way through the vein, entering into one wall and leaving out of the opposite wall of the vein. This state is shown in FIG. 5(e). In this state, as the internal needle 3 is removed, and the external needle 2 is retracted until the tip thereof is returned in the vein cavity 11, the blood is then found flowing backward again. If the external needle 2 is advanced again at this point of time, the treatment may happen to succeed, but in most cases, would fail as in the case of FIG. 5(d), as described above. Thus, another attempt to pierce into the vein will be needed at a different location on the skin.

As described above, referring to FIGS. 5(a) through 5(e), the indwelling intravenous needle of the conventional type tends to be associated with frequent failures because of various problems in vein piercing operation. The success in vein piercing largely depends on the skill and intuition of medical men performing vein piercing. The main reasons for this can be summarized as follows.

One reason is that there is a time lag in confirming the start of blood backflow at point P of the internal needle base $4_1$ after the cutting-edge tip 1 of the internal needle 3 has been pierced into the vein cavity 11 because the internal needle is made of a translucent metal.

The second reason is that even if only the cutting-edge tip 1 and the cutting edge root 6 remain in the vein cavity 11, blood backflow at point P of the internal-needle base $4_1$ is continued. In other words, since the indwelling intravenous needle of the conventional type relies solely on blood back-flow at point P for estimating the location of the cutting edge 1 of the internal needle 3 in the vein, despite the above-mentioned two structural defects, it is considerably uncertain to grasp the relative positions of the cutting edge and the vein cavity 11. In short, blood back-flow from the internal needle 3 does not necessarily pinpoint the exact location of the tip of the external needle 2. This makes it difficult to quickly pierce the external needle 2 into a proper location in the vein cavity.

SUMMARY OF THE INVENTION

This invention is intended to solve these problems. It is an object of this invention to enable medical men to properly, easily and safely give medical treatment using indwelling intravenous needles by providing two blood backflow passage routes on the internal needle 3 so that the back-flow of the blood in one route (groove) can be quickly observed visually so that the tip of the external needle 2 can be left at a proper location in the vein cavity.

DESCRIPTION OF THE PREFERRED EMBODIMENT

Figure 1A:
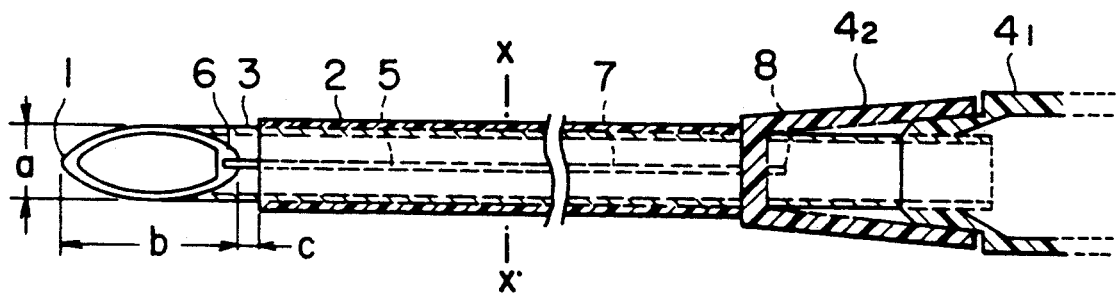
FIGS. 1(a)-(b) are of assistance in explaining an indwelling intravenous needle embodying this invention; (a) being an enlarged plan view illustrating an indwelling intravenous needle embodying this invention, and (b) being an enlarged sectional view substantially taken along line x—x in (a) above.
Figure 1B:
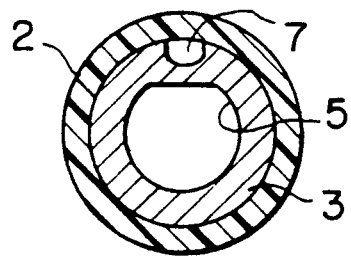
Figure 2:
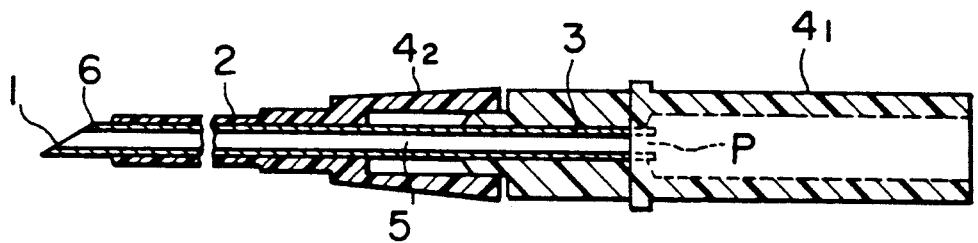
FIG. 2 is an enlarged sectional side view illustrating an indwelling intravenous needle of a conventional type.

Now, the construction of an embodiment of this invention will be described in detail. FIGS. 1(a)-(b) illustrate an indwelling intravenous needle embodying this invention; (a) being an enlarged plan view and (b) being an enlarged cross-sectional view substantially taken along line x—x in FIG. 1(a). Like parts are indicated by like numerals used in FIG. 2 described above. Those numerals relating to the characteristics of the construction of this invention are as follows: Numeral 7 refers to a groove formed in the longitudinal direction, starting from the cutting edge root 6, and numeral 8 refers to an end of the groove 7. The connection between the internal needle base $4_1$ and the external needle base $4_2$ is not gas-tight because blood can easily flow into the groove 7. Numeral 9 in FIGS. 3 and 4 refers to the skin, 10 to the vein wall and 11 to the vein cavity, respectively.

Figure 3:
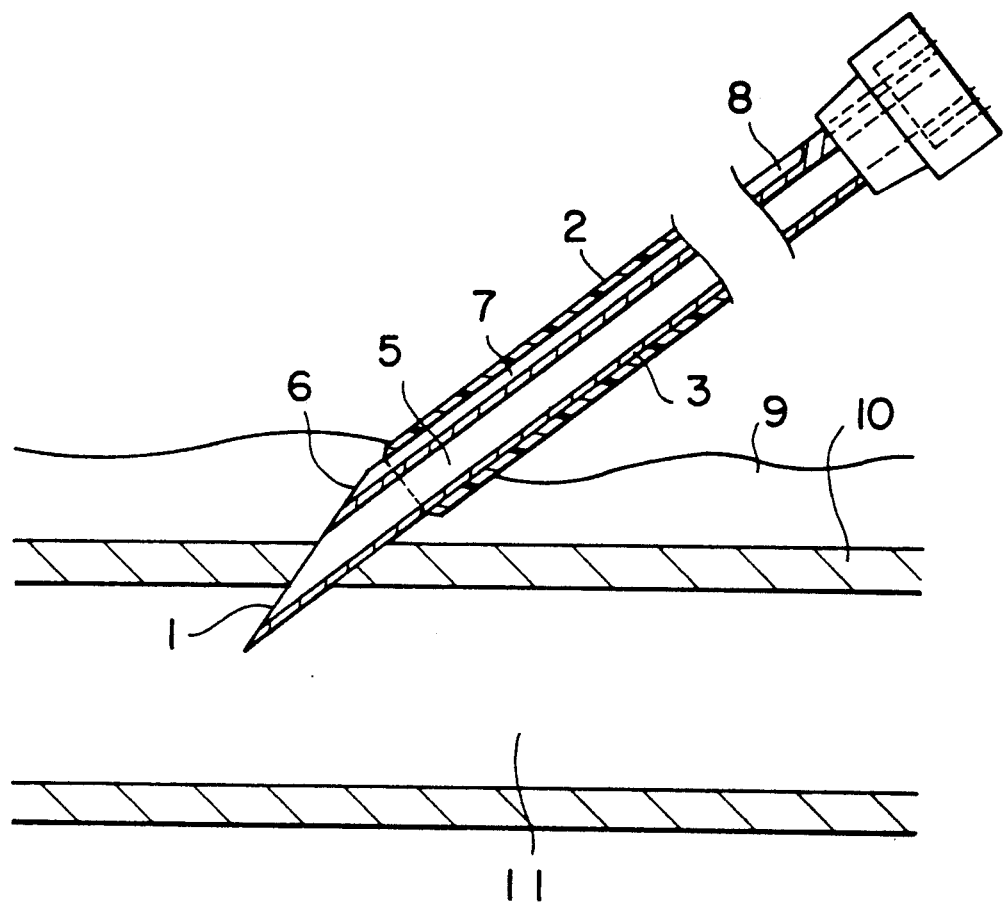
FIG. 3 is an enlarged sectional side view illustrating the state where only the tip of the cutting edge of the indwelling intravenous needle of this invention is pierced into the vein cavity through the skin.

The mode of operation and effects of this invention having the aforementioned construction will be described in the following, referring to the accompanying drawings. FIG. 3 is an enlarged sectional side view illustrating the state where only the cutting-edge tip 1 of the indwelling intravenous needle is pierced through the skin 9 into the vein cavity 11. As the cutting-edge tip 1 of the internal needle 3 is pierced into the vein cavity 11, the back-flow of the blood is caused in the internal-needle bore 5, as in the case of the indwelling intravenous needle of the conventional type. This is confirmed by the fact that the blood backflow is observed at point P of the internal-needle base $4_1$ (refer to FIG. 2). Thus, it is confirmed that the indwelling intravenous needle has been pierced into the vein in a proper direction, and that it is now sufficient to advance the cutting edge only by the length of the cutting edge at most.

Figure 4:
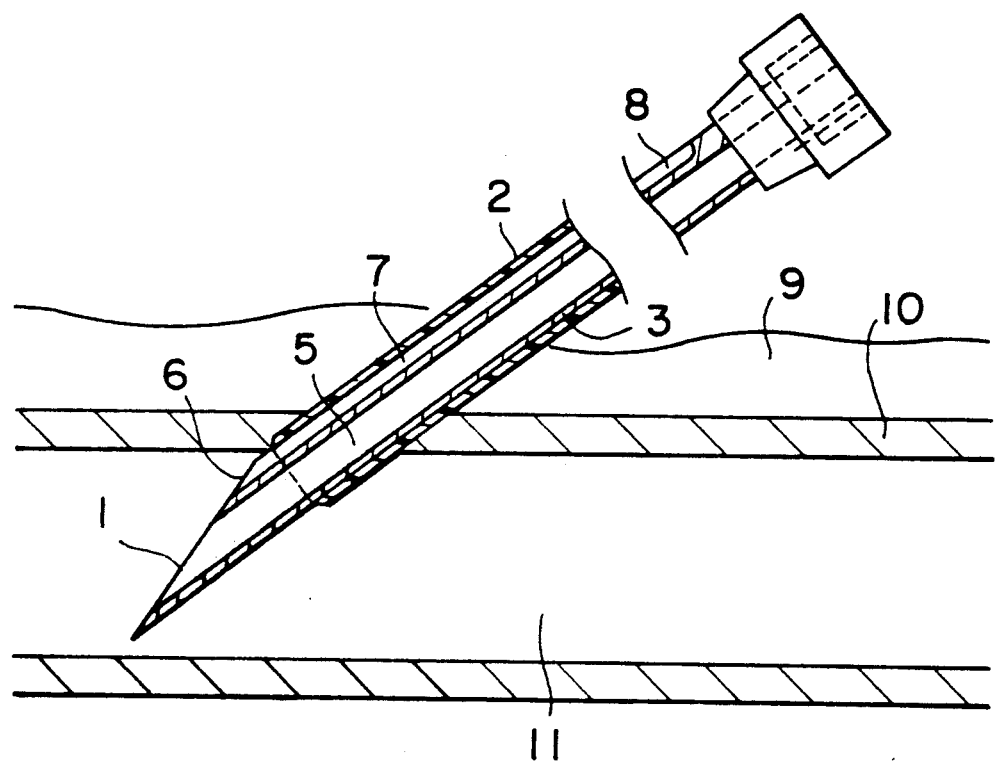
FIG. 4 is an enlarged sectional side view illustrating the state where the whole of the cutting edge, including the port of the groove of the indwelling intravenous needle of this invention is pierced properly into the vein cavity through the skin.
Figure 5:
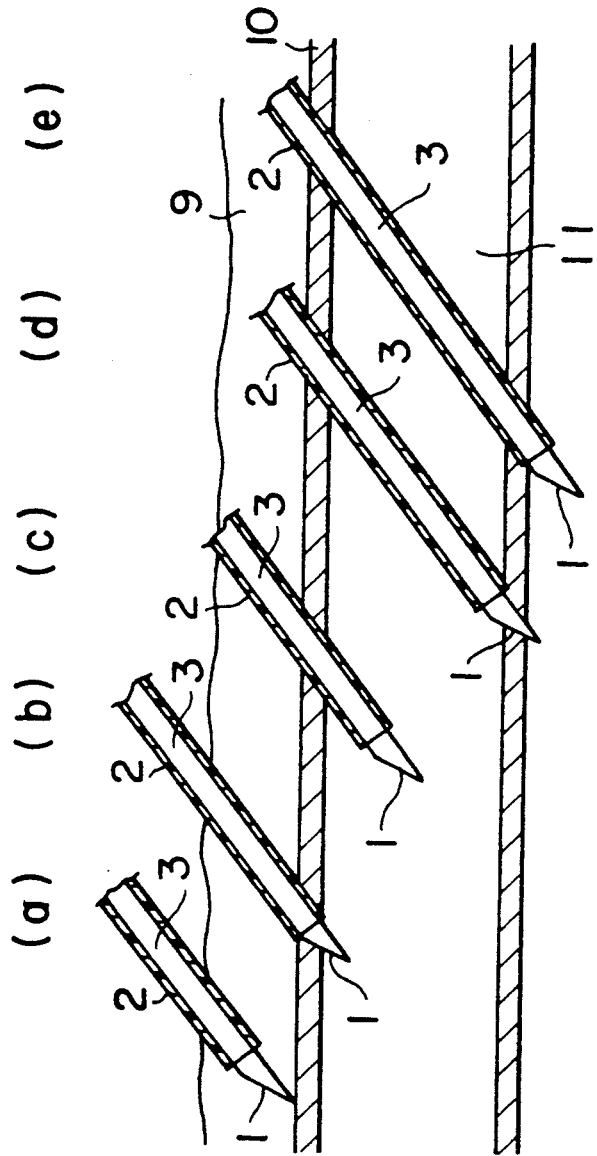
FIGS. 5(a)-(e) illustrate a schematic side view of assistance in explaining various problems encountered when an indwelling intravenous needle of a conventional type is pierced into the blood vessel; (a) and (e) showing the state where the needle is pierced outside the blood vessel, (b) and (d) showing the state where the needle is pierced imperfectly, and (c) showing the ideal state of the needle pierced into the blood vessel.

The indwelling intravenous needle of this invention includes the groove 7 formed on the cutting edge root 6 and the external needle 2 made of a transparent or translucent synthetic resin covering the internal needle 3. When the needle is further pierced into the vein cavity 11 up to the cutting edge root 6, as shown in FIG. 4, the blood back-flow in the groove 7 formed on the surface of the internal needle 3 can be visually observed from the initial stage to confirm that the tip of the external needle 2 reaches inside the vein cavity 11 or at least inside the vein wall 10.

Then, the external needle 2 can be positively placed in the vein cavity 11 by extracting the internal needle 3 after the entire indwelling intravenous needle is pierced a little further (the length C in FIG. 1).

As described above, the indwelling intravenous needle of this invention, having the bore 5 and the groove 7 in the internal needle thereof as inlets of the blood flowing back as the needle is pierced into the vein, makes it possible to accurately estimate the relative positions of the tip of the external needle 2 to be retained in the vein cavity and the vein cavity, so one can perform the vein piercing operation accurately, easily and safely.

Typical parameters for the external and internal needles of commercially available indwelling intravenous needles will be given below, referring to FIG. 1.

Inside diameter a of the external needle 2: 0.47-1.30 mm

Length b of the cutting edge of the internal needle 3: 1.5-3.3 mm

Difference c between the tips of the cutting edge root 6 and the external needle 2: 0.2-0.5 mm Test results indicate that the difference between the tips of the cutting edge root 6 and the external needle 2 should preferably be as close as possible to 0 mm. Taking into account the above-mentioned parameters of commercially available indwelling intravenous needles, therefore, the best results can be accomplished with the needle having the difference c of 0.2 mm.

Although the groove 7 is drawn exaggeratedly in the figures to facilitate understanding, sufficient blood backflow can be insured with a groove having a width of less than 0.2 mm and a depth of 0.05 mm. The groove 7 on the surface of the internal needle can be machined directly on the internal needle of an indwelling intravenous needle of a conventional type.

Needless to say, there can be a large number of variations in the width, depth and shape of the groove 7, depending on the size, material, etc. of the indwelling intravenous needle.

What is claimed is:

1. An indwelling intravenous needle comprising:

a hollow internal metal needle having at one end, a beveled cutting edge having a root and being connected at the other end, to a tip of a cylindrical base made of a transparent synthetic resin and said internal needle having a groove located on the outer circumferential surface of said internal needle, said groove extending longitudinally from said root to the area where said internal needle is connected to said base;

said internal needle having an inner bore which is defined by the internal surface; and a hollow external needle made of a synthetic resin and having a transparent base for visualizing blood backflow, said external needle having an end that is slidably fittable onto the outer surface of said internal needle up to an area near the root and another end comprising said base that is flared to fit onto the tip of the internal needle base.

2. An indwelling intravenous needle comprising:

a hollow internal metal needle having at one end, a beveled cutting edge having a root and being connected at the other end to a tip of a cylindrical base made of a translucent synthetic resin and said internal needle having a groove located on the outer circumferential surface of said internal needle, said groove extending longitudinally from said root to an area where said internal needle is connected to said base;

said internal needle having an inner bore which is defined by the internal surface; and a hollow external needle made of synthetic resin and having a translucent base for visualizing blood back flow, said external needle having an end that is slidably fittable onto the outer surface up to an area near the root and another end comprising said base that is flared to fit on to the tip of the internal needle base.

* * * * *